(12) United States Patent
Biggadike

(10) Patent No.: US 6,750,210 B2
(45) Date of Patent: *Jun. 15, 2004

(54) FORMULATION CONTAINING NOVEL ANTI-INFLAMMATORY ANDROSTANE DERIVATIVE

(75) Inventor: Keith Biggadike, Stevanage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 26 days.

This patent is subject to a terminal disclaimer.

(21) Appl. No.: 10/066,964

(22) Filed: Feb. 4, 2002

(65) Prior Publication Data
US 2002/0173496 A1 Nov. 21, 2002

Related U.S. Application Data

(63) Continuation-in-part of application No. 09/958,050, filed as application No. PCT/GB01/03495 on Aug. 3, 2001.

(30) Foreign Application Priority Data
Aug. 5, 2000 (GB) .............................. 0019172

(51) Int. Cl.$^7$ .......................... A61K 31/58; C07J 17/00
(52) U.S. Cl. ...................................... 514/172; 540/114
(58) Field of Search ................... 540/114; 514/172

(56) References Cited

U.S. PATENT DOCUMENTS

| | | | |
|---|---|---|---|
| 3,067,197 A | 12/1962 | Agnello et al. | |
| 3,639,434 A | 2/1972 | Oxley et al. | |
| 3,828,080 A | 8/1974 | May et al. | |
| 3,856,828 A | 12/1974 | Phillips et al. | |
| 3,981,894 A | 9/1976 | Phillips et al. | |
| 3,989,686 A | 11/1976 | Phillips et al. | |
| 4,093,721 A | 6/1978 | Phillips et al. | |
| 4,187,301 A | 2/1980 | Edwards | |
| 4,188,385 A | 2/1980 | Edwards | |
| 4,198,403 A | 4/1980 | Alvarez | |
| 4,261,984 A | 4/1981 | Alvarez | |
| 4,263,289 A | 4/1981 | Edwards | |
| 4,267,173 A | 5/1981 | Draper | |
| 4,285,937 A | 8/1981 | Kalvoda | |
| 4,310,466 A | 1/1982 | Edwards | |
| 4,335,121 A | 6/1982 | Phillipps et al. | |
| 4,377,575 A | 3/1983 | Stache et al. | |
| 4,472,393 A | 9/1984 | Shapiro | |
| 4,607,028 A | 8/1986 | Schmidlin | |
| 4,710,495 A | 12/1987 | Bodor | |
| 4,861,765 A | 8/1989 | Mitsukuchi et al. | |
| 4,992,474 A | 2/1991 | Skidmore et al. | |
| 4,994,439 A | 2/1991 | Longenecker et al. | |
| 4,996,335 A | 2/1991 | Bodor | |
| 5,250,293 A | 10/1993 | Gleich | |
| 5,420,120 A | 5/1995 | Boltralik | |
| 5,658,549 A | 8/1997 | Akehurst et al. | |
| 5,707,984 A | 1/1998 | Tjoeng et al. | |
| 5,837,699 A | 11/1998 | Sequeira et al. | |
| 5,849,265 A | 12/1998 | Li-Bovet et al. | |
| 5,889,015 A | 3/1999 | Sequeira et al. | |
| 5,919,776 A | 7/1999 | Hagmann et al. | |
| 5,972,920 A | 10/1999 | Seidel | |
| 5,981,517 A | 11/1999 | Bodor | |
| 6,057,307 A | 5/2000 | Sequeira et al. | |
| 6,127,353 A | 10/2000 | Yuen et al. | |
| 6,136,294 A | 10/2000 | Adjei et al. | |
| 6,197,761 B1 | 3/2001 | Biggadike et al. | |
| 6,261,539 B1 * | 7/2001 | Adjei et al. | .................. 424/46 |
| 6,395,300 B1 | 5/2002 | Straub et al. | |
| 6,537,983 B1 | 3/2003 | Biggadike et al. | |

FOREIGN PATENT DOCUMENTS

| | | |
|---|---|---|
| DE | 2336693 | 2/1975 |
| DE | 2538569 | 3/1977 |
| EP | 0004773 | 10/1979 |
| EP | 0057401 | 8/1982 |
| EP | 0135476 | 3/1985 |
| EP | 0179583 | 4/1986 |
| EP | 0416951 | 3/1991 |
| EP | 0418716 | 3/1991 |

(List continued on next page.)

OTHER PUBLICATIONS

Phillips, G.H., et al., "Synthesis and Structure–Activity Relationships in a series of Antiinflammatory Corticosteroid Analogues, Halomethyl Androstane–17β–carbothioates and– 17–β–carboselenoates," Journal of Medicinal Chemistry 1994, 37, 3717–3729.

U.S. patent application No.: 09/958,050 filed on Oct. 2, 2001.

U.S. patent application No.: 10/067,020 filed on Feb. 4, 2002.

(List continued on next page.)

*Primary Examiner*—Barbara P. Badio
(74) *Attorney, Agent, or Firm*—James P. Riek

(57) ABSTRACT

There is provided a pharmaceutical aerosol formulation comprising (i) a compound of formula (I)

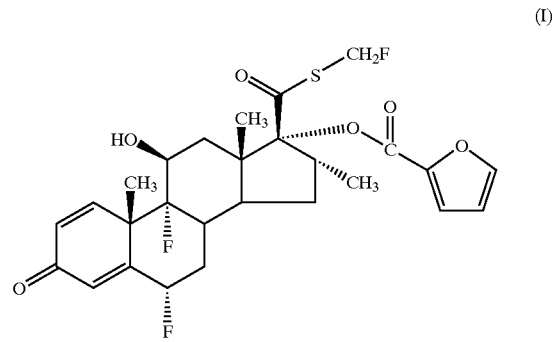

(I)

or a solvate thereof as medicament, (ii) a liquified hydrofluoroalkane (HFA) gas as propellant; and characterized in that the compound of formula (I) or a solvate thereof is completely dissolved in the formulation.

19 Claims, No Drawings

FOREIGN PATENT DOCUMENTS

| | | |
|---|---|---|
| EP | 0521455 | 1/1993 |
| EP | 0640616 | 3/1995 |
| EP | 0646593 | 4/1995 |
| FR | 580494 | 10/1986 |
| GB | 1384372 | 2/1975 |
| GB | 1438940 | 6/1976 |
| GB | 1517278 | 7/1978 |
| GB | 2079755 | 1/1982 |
| GB | 2140800 | 12/1984 |
| IL | 109656 | 2/1998 |
| JP | 04208267 | 7/1992 |
| WO | 92/14472 | 9/1992 |
| WO | 94/21229 | 9/1994 |
| WO | 9421229 | 9/1994 |
| WO | 95/31964 | 11/1995 |
| WO | 96/19199 | 6/1996 |
| WO | 97/05136 | 2/1997 |
| WO | 97/15298 | 5/1997 |
| WO | 97/24365 | 7/1997 |
| WO | 97/46243 | 12/1997 |
| WO | 98/17676 | 4/1998 |
| WO | 98/34596 | 8/1998 |
| WO | 98/43630 | 10/1998 |
| WO | 99/01467 | 1/1999 |
| WO | 99/25359 | 5/1999 |
| WO | 99/32089 | 7/1999 |
| WO | 00/16814 | 3/2000 |
| WO | 00/33892 | 6/2000 |
| WO | 00/38811 | 7/2000 |
| WO | 00/57401 | 8/2000 |
| WO | 01/04118 | 1/2001 |
| WO | 01/15744 | 3/2001 |
| WO | 01/20331 | 3/2001 |
| WO | 01/54664 | 8/2001 |
| WO | 01/62722 | 8/2001 |
| WO | 01/78736 | 10/2001 |
| WO | 01/78739 | 10/2001 |
| WO | 01/78741 | 10/2001 |
| WO | 01/78745 | 10/2001 |
| WO | 02/00199 | 1/2002 |
| WO | 02/00679 | 1/2002 |
| WO | 02/007767 | 1/2002 |
| WO | 02/008243 | 1/2002 |
| WO | 0212265 | 2/2002 |
| WO | 0212266 | 2/2002 |
| WO | 02/013868 | 2/2002 |
| WO | 02/26723 | 4/2002 |
| WO | 02/053186 | 7/2002 |
| WO | 02/066422 | 8/2002 |
| WO | 02/070490 | 9/2002 |
| WO | 02/076933 | 10/2002 |
| WO | 02/085296 | 10/2002 |
| WO | 02/088167 | 11/2002 |
| WO | 02/100879 | 12/2002 |
| WO | 03/013427 | 2/2003 |
| WO | 03/033000 | 4/2003 |
| WO | 03/035668 | 5/2003 |
| WO | 03/040691 | 5/2003 |
| WO | 03/042229 | 5/2003 |
| WO | 03/042230 | 5/2003 |
| ZA | 872389 | 4/1987 |

OTHER PUBLICATIONS

U.S. patent application No.: 10/067,010 filed on Feb. 4, 2002.

U.S. patent application No.: 10/066,836 filed on Feb. 4, 2002.

U.S. patent application No.: 10/200,364 filed on Jul. 22, 2002.

U.S. patent application No.: 10/281,735 filed on Oct. 28, 2002.

U.S. patent application No.: 10/241,658 filed on Sep. 11, 2002.

U.S. patent application No.: 10/066,951 filed on Feb. 4, 2002.

Janette M. Mahoney et al., "Drug effects on the neovascularization response to silver nitrate cauterization of the rat cornea" Current Eye Research, vol. 4, No. 5, 1985, pp. 531–535.

Richard A. Kenley et al., "An Automated, Column–Switching HPLC Method for Analyzing Active and Excipient Materials in Both Cream and Ointment Formulations," Drug Development and Industrial Pharmacy, vol. 11 (9&10), 1985, pp. 1781–1796.

R. Woodford et al., "Activity and bioavailability of a new steroid (Timobesone acetate) in cream and ointment compared with Lidex and Dermovate creams and ointments and Betnovate cream" Int'l Journal of Pharmaceutics, vol. 26 (1985) pp. 145–155.

Denis J. Kertesz et al., "Thiol Esters from Steroid 17β–Carboxylic Acids: Carboxylate Activation and Internal Participation by 17 α–Acylates" J. Org. Chem., vol. 51, 1986, pp. 2315–2328.

Popper, T.L., et al., "Structure–Activity Relationship of a series of novel topical corticosteroids", Journal of Steroid Biochemistry 1987, 837–843.

John T. H. Ong et al., "Micellar Solubilization of Timobesone Acetate in Aqueous and Aqueous Propylene Glycol Solutions of Nonionic Surfactants", Pharmaceutical Research, vol. 5, No. 11, 1988, pp. 704–708.

John T. H. Ong et al., Intrinsic Potencies of Novel Thiol Ester Corticosteroids RS–85095 and RS–21314 as Compared With Clobetasol 17–Propionate and Fluocinonide Arch Dermatol, vol. 125, Dec. 1989, pp. 1662–1665.

Isogai, Mitsutaka, et al., "Binding affinities of Mometasone Furoate and related compounds including its Metabolites for the Glucocorticoid Receptor of Rat Skin Tissue" J. Steroid Biochem. Mol. Biol. 1993, 141–145.

S.J. Lane et al., "Evaluation of a New Capillary Electrochromatography/Mass Spectrometry Interface Using Short Columns and High Field Strengths for Rapid and Efficient Analyses," Rapid Communications in Mass Spectrometry, vol. 10, 1996, pp. 733–736.

Franklin I. Aigbirhio et al., "Automated Radiosynthesis of No–carrier–added [S–*fluoromethyl*–$^{18}$F]Fluticasone Propionate as a Radiotracer for Lung Deposition Studies with PET" Journal of Labelled Compounds and Radiopharmaceuticals, vol. 39, No. 7, 1997, pp. 569–584.

Nisha Mistry et al., "Characterisation of impurities in bulk drug batches of fluticasone propionate using directly coupled HPLC–NMR spectroscopy and HPLC–MS," Journal of Pharmaceutical and Biomedical Analysis vol. 16, 1997, pp. 697–705.

Nisha Mistry et al., Impurity profiling in bulk pharmaceutical batches using 19F NMR spectroscopy and distinction between monomeric and dimeric impurities by NMR–based diffusion measurements, Journal of Pharmaceutical and Biomedical Analysis, vol. 19, 1999, pp. 511–517.

N. Smith et al., "Comparison of the electroosmotic flow profiles and selectivity of stationary phases used in capillary electrochromatography," Journal of Chromatography A., vol. 832, 1999, pp. 44–54.

R.C. Garner et al., "A validation study comparing accelerator MS and liquid scintillation counting for analysis of $^{14}$C–labelled drugs in plasma, urine and faecal extracts", Journal of Pharmaceutical and Biomedical Analysis vol. 24, 2000, pp. 197–209.

Harold S. Nelson et al., "Fluticasone propionate/salmeterol combination provides more effective asthma control than low–dose inhaled corticosteroid plus montelukast," J. Allergy Clin. Immunol., vol. 106, No. 6, Dec. 2000, pp. 1088–1095.

Gunnar Johansson et al., "Comparison of Salmeterol/Fluticasone Propionate Combination With Budesonide in Patients With Mild–to–Moderate Asthma" Clin. Drug Invest. vol. 21, No. 9, 2001, pp. 633–642.

Bertil Pettersson et al., Re–evaluation of the classical Mycoplasma lipophilum cluster (Weisburg et al. 1989) and description of two new clusters in the hominis group based on 16S rDNA sequences, Int'l Journal of Systematic & Evolutionary Microbiology (2001) vol. 51, pp. 633–643.

Sarah A. Lewis et al., "Association of specific allergen sensitization with socioeconomic factors and allergic disease in a population of Boston women", J. Allergy Clin. Immunol., vol. 107, No. 4, Apr. 2001, pp. 615–622.

Katherine A. Lyseng–Williamson et al., "Inhaled Salmeterol/Fluticasone Propionate Combination In Chronic Obstructive Pulmonary Disease," Am. J. Respir. Med. vol. 1, No. 4, 2002, pp. 273–282.

Jeffrey W. Millard et al., "Solubilization by cosolvents Establishing useful constants for the log–linear model," Int'l Journal of Pharmaceutics vol. 245, 2002, pp. 153–166.

C. Baumgarten et al., "Initial Treatment of Symptomatic Mild to Moderate Bronchial Asthma with the Salmeterol/Fluticasone Propionate (50/250µg) Combination Product (SAS 40023)" European Journal of Medical Research 2002, vol. 7, pp. 1–7.

Stephen J. Fowler et al., "Step–down therapy with low–dose fluticasone–salmeterol combination or medium–dose hydrofluoroalkane 134a–beclomethasone alone" J. Allergy Clin. Immunol., vol. 109, No. 6, Jun. 2002, pp. 929–935.

Elizabeth F. Juniper et al., "Impact of Inhaled Salmeterol/Fluticasone Propionate Combination Product versus Budesonide on the Health–Related Quality of Life of Patients with Asthma," Am. J. Respir. Med., vol. 1, No. 6, 2002, pp. 435–440.

William Busse et al., "Steroid–sparing effects of fluticasone propionate 100 µg and salmeterol 50 µg administered twice daily in a single product in patients previously controlled with fluticaasone propionate 250 µg administered twice daily" J. Allergy Clin. Immunol., vol. 111, No. 1, Jan. 2003, pp. 57–65.

Ueno H et al, "Synthesis and Evaluation of Antiinflammatory Activities of a Series of Corticosteroid 17. Alpha–Esters Containing a Functional Group" ,Journal of Medicinal Chemistry, American Chemical Society, vol. 34, No. 8, Aug. 1991, pp. 2468–2473.

Peter J Barnes, "Novel approaches and targets for treatment of Chronic Obstructive Pulmonary Disease" American Journal of Respiratory and Critical Care Medicine, vol. 160, 1999, pp. S72–S79.

B.J. O Conner: "Combination Therapy", Pulmonary Pharmacology and Therapeutics, vol. 11, No. 5/6, 1998, pp. 397–399.

Peter J Barnes, "Chronic Obstructive Pulmonary Disease: new opportunities for drug development" Trends in Pharmacological Sciences, Elsevenir Trends Journal, vol. 19, No. 10, 1998, pp. 415–423.

Simon Bowler,"Long acting beta agonists", Australian Family Physician,vol. 27, No. 12, 1998, pp. 1114–1118.

Naedle–Risha R et al, "Dual components of optimal asthma therapy: scientific and clinical rationale for the use of long acting beta–agonists with inhaled corticosteroids", The Journal of the American Osteopathic Association, vol. 101, No. 9, Sep. 2001, pp. 2001–2009.

T Van Der Molen et al, "Effects of the Long Acting Beta Agonist Formoterol on Asthma Control in Asthmatic Patients Using Inhaled Corticosteroids", vol. 52, No. 6, 1997, pp. 535–539.

B.N. Lutsky et al., "A Novel Class of potent Topical Anti–inflammatory Agents: 17 Benzoylated, 7—Halogeno Substituted Corticosteroids", Arzeneimittel Forschung, vol. 29, No. 11, Nov. 1979, pp. 1662–1667.

Peter J. Barnes, "Efficacy of Inhaled Corticosteroids in Asthma", The Journal of Allergy and Clinical Immunology, vol. 102, No. 4, pp. 531–538.

U.S. Publication No. 2002/0081266 publ. On Jun. 27, 2002.

U.S. Publication No. 2002/0103392 publ. On Aug. 1, 2002.

U.S. Publication No. 2002/0165211 publ. on Nov. 7, 2002.

U.S. Publication No. 2002/0173496 publ. on Nov. 21, 2002.

U.S. Publication No. 2002/0177581 publ. on Nov. 28, 2002.

U.S. Publication No. 2003/0073676 publ. on Apr. 17, 2003.

U.S. Publication No. 2003/0109511 publ. on Jun. 12, 2003.

U.S. Publication No. 2003/0144257 publ. on Jul. 31, 2003.

U.S. Publication No. 2003/0158163 publ. on Aug. 21, 2003.

Knobil, K., et al., "Adding Salmeterol is More Effective Than Increasing the Dose of Fluticasone for Patients With Asthma Who are Symptomatic on Low Dose Fluticasone," European Respiratory Review, Copenhagen, DK, vol. 12, No. Suppl 29, Dec. 1998 (1998–12), pp. 19S–20S, XP000992769.

Shapiro, E.L., et al., "17 Heteroaroyl Esters of Corticosteroids 2. 11–Beta Hydroxy Series," Journal of Medicinal Chemistry, American Chemical Society, Washington, US, vol. 30, No. 9, 1987, pp. 1581–1588, XP002153839.

* cited by examiner

FORMULATION CONTAINING NOVEL ANTI-INFLAMMATORY ANDROSTANE DERIVATIVE

"This application is a Continuation-in-part of U.S. patent application Ser. No. 09/958,050 filed on Oct. 2, 2001, a U.S. National Stage filing under 35 USC 371 of International Patent Application No. PCT/GB01/03495 filed Aug. 3, 2001, which claims priority to United Kingdom Patent Application No. GB 0019172.6 filed Aug. 5, 2000."

The present invention relates to a pharmaceutical formulation containing novel anti-inflammatory and anti-allergic compound of the androstane series and to processes for its preparation. The present invention also relates to therapeutic uses thereof, particularly for the treatment of inflammatory and allergic conditions.

Glucocorticoids which have anti-inflammatory properties are known and are widely used for the treatment of inflammatory disorders or diseases such as asthma and rhinitis. For example, U.S. Pat. No. 4,335,121 discloses 6α, 9α-Difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern steroids are very much safer than those originally introduced, it remains an object of research to produce new molecules which have excellent anti-inflammatory properties, with predictable pharmacokinetic and pharmacodynamic properties, with an attractive side effect profile, and with a convenient treatment regime.

We have now identified a novel glucocorticoid compound and formulation thereof which substantially meets these objectives.

Thus, according to one aspect of the invention, there is provided a pharmaceutical aerosol formulation comprising (i) a compound of formula (I).

Thus, according to one aspect of the invention, there is provided a pharmaceutical aerosol formulation comprising (i) a compound of formula (I)

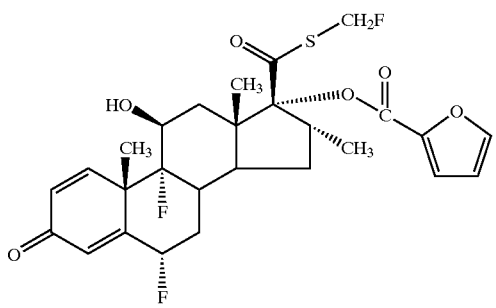

(I)

or a solvate thereof as medicament, (ii) a liquified hydrofluoroalkane (HFA) gas as propellant; and characterised in that the compound of formula (I) or a solvate thereof is completely dissolved in the formulation.

The chemical name of the compound of formula (I) is 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester.

References hereinafter to the compound according to the invention include both the compound of formula (I) and solvates thereof, particularly pharmaceutically acceptable solvates.

The compound of formula (I) and formulations thereof have potentially beneficial anti-inflammatory or anti-allergic effects, particularly upon topical administration to the lung or nose, demonstrated by, for example, its ability to bind to the glucocorticoid receptor and to illicit a response via that receptor, with long acting effect. Hence, the compound of formula (I) is useful in the treatment of inflammatory and/or allergic disorders, especially in once-per-day therapy.

The efficiency of an aerosol device, such as an MDI, is a function of the dose deposited at the appropriate site in the lungs. Deposition is affected by several factors, of which one of the most important is the aerodynamic particle size. Solid particles and/or droplets in an aerosol formulation can be characterised by their mass median aerodynamic diameter (MMAD, the diameter around which the mass aerodynamic diameters are distributed equally).

Particle deposition in the lung depends largely upon three physical mechanisms:

1. impaction, a function of particle inertia;
2. sedimentation due to gravity; and
3. diffusion resulting from Brownian motion of fine, submicrometer (<1 μm) particles.

The mass of the particles determines which of the three main mechanisms predominates.

The effective aerodynamic diameter is a function of the size, shape and density of the particles and will affect the magnitude of forces acting on them. For example, while inertial and gravitational effects increase with increasing particle size and particle density, the displacements produced by diffusion decrease. In practice, diffusion plays little part in deposition from pharmaceutical aerosols. Impaction and sedimentation can be assessed from a measurement of the MMAD which determines the displacement across streamlines under the influence of inertia and gravity, respectively.

Aerosol particles of equivalent MMAD and GSD (geometric standard deviation) have similar deposition in the lung irrespective of their composition. The GSD is a measure of the variability of the aerodynamic particle diameters.

For inhalation therapy there is a preference for aerosols in which the particles for inhalation have a diameter of about 0.5 to 51 μm. Particles which are larger than 5 μm in diameter are primarily deposited by inertial impaction in the orthopharynx, particles 0.5 to 5 μm in diameter, influenced mainly by gravity, are ideal for deposition in the conducting airways, and particles 0.5 to 3 μm in diameter are desirable for aerosol delivery to the lung periphery. Particles smaller than 0.5 μm may be exhaled.

In suspension formulations, particle size in principle is controlled during manufacture by the size to which the solid medicament is reduced, usually by micronisation. However, if the suspended drug has the slightest solubility in propellant, a process known as Ostwald Ripening can lead to particle size growth. Also, particles may have a tendency to aggregate, adhere to or diffuse into parts of the MDI eg. canister or valve. The effect of Ostwald ripening and particularly of drug deposition may be particularly severe for potent drugs which need to be formulated in low doses. Solution formulations do not suffer from these disadvantages since the particle size is defined by the function of rate of evaporation of the propellant from the formulation, and the time between release of formulation from canister, solute (e.g. drug and/or excipient) concentration and the moment of inhalation.

In the case of administration of formulations to the nose, ciliary clearance is very rapid and drug delivered by means of suspension formulations may be cleared by the cilia before it has had the opportunity to dissolve and enter the target cells of the target organ. Thus a solution formulation has advantages since it speeds up absorption thus affording the active ingredient a greater opportunity to exert a therapeutic effect before ciliary clearance takes place. This may also lead to faster onset of action.

The aerosol formulation may be delivered from a pressurised pack, such as a metered dose inhaler. The preferred hydrofluoroalkane propellants are 1,1,1,2-tetrafluoroethane, 1,1,1,2,3,3,3-heptafluoro-n-propane and mixtures thereof, most especially 1,1,1,2-tetrafluoroethane.

The formulation according to the invention will generally contain a solubilising agent to aid solubilisation of the compound of formula (I) or a solvate thereof in the formulation.

In a first embodiment of the invention the solubilising agent is a hydroxy containing co-solvent liquid such ethanol or a glycol eg propylene glycol (eg PEG200, PEG400), propylene glycol, especially ethanol.

Such a solubilising agent will generally be employed in an amount of 5–20% depending on the particular solubilising agent and the amount of compound of formula (I) needing to be solubilised. In the case of ethanol, and amount of 5–15 especially 5–10% is generally suitable.

In a particularly preferred aspect of this embodiment, the formulation also contains a low volatility component to increase the mass median aerodynamic diameter (MMAD) of the aerosol particles on actuation of the inhaler.

The presence of the low volatility component in the solution formulation increases the fine particle mass (FPM) as defined by content of stages 3–5 of an Andersen Cascade Impactor on actuation of the formulation relative to solution formulations which omit this component. Solution formulations which omit the low volatility component generally give rise to a particle size distribution which has a higher content of fine particles.

The preferred low volatility component is glycerol, propylene glycol or polyethylene glycol eg PEG200, PEG400), especially glycerol. Polyethylene glycol is also of particular interest, especially PEG400. Preferably the low volatility component is employed in an amount of 0.5–3% w/w (based on weight of formulation) especially around 0.5–1.5% w/w eg around 1% w/w.

Thus more particularly an aspect of the invention can be defined as a pharmaceutical aerosol formulation comprising (i) a compound of formula (I)

(I)

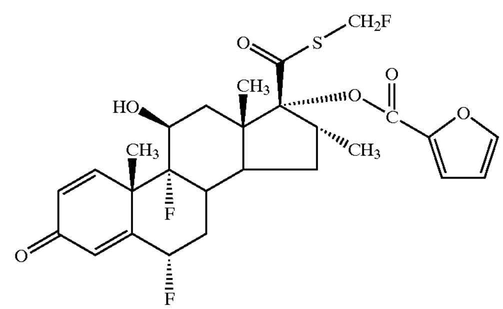

or a solvate thereof as medicament, (ii) 1,1,1,2-tetrafluoroethane as propellant, (iii) a solubilising agent (especially ethanol) to assist the solubilisation of the medicament in the propellant and (iv) optionally (and preferably) a low volatility component (especially glycerol); characterised in that the compound of formula (I) or a solvate thereof is completely dissolved in the formulation.

In a second and more preferred embodiment of the invention the solubilising agent is an oligolactic acid or derivative thereof.

Examples of oligolactic acids and derivatives thereof, and methods for their preparation, are described in WO94/21229. Oligolactic acids are oligomers of lactic acid (either in racemic or single enantiomeric form i.e. L-lactic acid) containing an average of n repeat units in the oligomer distribution and have the general formula given in structure (II) below:

$$H-[O-CH(CH_3)-CO]_n-OH \quad (II)$$

Typically oligolactic acids are polydispersed with average values for n between 3 and 20 especially between 3 and 15.

Preferred derivatives of oligolactic acids include compounds in which hydroxy end of the oligomer is acylated for example with an acetyl group to give a compound of formula (IIA):

$$CH_3-CO-[O-CH(CH_3)-CO]_n-OH \quad (IIA)$$

Further derivatives of oligolactic acids include those in which the —COOH terminus is derivatised instead or in addition to the —OH terminus. Optionally the —COOH terminus is derivatised in addition to the —OH terminus. For example the —COOH terminus may be transformed into an amide moiety for example by amidation with an amino acid, for example one of the 20 naturally occurring amino acids, especially glycine. The amino acid may be employed as a racemate although it is preferable to employ it as the naturally occurring L-enantiomer.

Also salts of the acid (eg potassium, sodium, ammonium salts etc) are included.

The oligolactic acid or derivative thereof will typically be employed at a concentration of up to 10% w/w based on weight of formulation, eg 0.1–6% especially 0.5–5% w/w. The oligolactic acid or derivative thereof should also be completely dissolved in the formulation.

Typically the oligolactic acid or derivative thereof will be employed in an amount relative to the amount of drug (based on weight) of 0.5:1 to 1:100, especially 2:1 to 100:1, particularly 10:1 to 50:1.

The formulation may also contain other formulation excipients, for example a co-solvent eg a hydroxy containing liquid co-solvent such as ethanol or a glycol (eg propylene glyol or a polyethylene glycol eg PEG200 or PEG400) to increase the solublity of the compound of formula (I) in the propellant. However since the oligolactic acid or derivative thereof is capable of dissolving the compound of formula (I) in the propellant without use of cosolvents, preferably the formulation is free of co-solvents especially ethanol.

Pressurised formulations will generally be retained in a canister (eg an aluminium canister) closed with a valve (eg a metering valve) and fitted into an actuator provided with a mouthpiece.

Canisters generally comprise a container capable of withstanding the vapour pressure of the HFA propellant, such as plastic or plastics coated glass bottle or preferably a metal can, for example an aluminium can which may optionally be anodised, lacquer-coated and/or plastics coated, which container is closed with a metering valve. It may be preferred that canisters be coated with a fluorocarbon polymer as described in WO 96/32151, for example, a co-polymer of polyethersulphone (PES) and polytetrafluoroethylene (PTFE). Another polymer for coating that may be contemplated is FEP (fluorinated ethylene propylene). The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Thermoplastic elastomer valves as described in WO92/11190 and valves containing EPDM rubber as described in WO95102651 are especially suitable. Suitable valves are commercially available from manufacturers well known in the aerosol industry, for example, from Valois, France (eg. DF10, DF30, DF60), Bespak pic, UK (eg. BK300, BK356, BK357) and 3M-Neotechnic Ltd, UK (eg. Spraymiser™). The DF31 valve of Valois, France is also suitable.

Valve seals, especially the gasket seal, will preferably be manufactured of a material which is inert to and resists extraction into the contents of the formulation, especially when the contents include ethanol.

Valve materials, especially the material of manufacture of the metering chamber, will preferably be manufactured of a material which is inert to and resists distortion by contents of the formulation, especially when the contents include ethanol. Particularly suitable materials for use in manufacture of the metering chamber include polyesters eg polybutyleneterephthalate (PBT) and acetals, especially PBT.

Materials of manufacture of the metering chamber and/or the valve stem may desirably be fluorinated, partially fluorinated or impregnated with fluorine containing substances in order to resist drug deposition.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The formulation containing the medicament, propellant and any other formulation ingredients is pressure filled through the charge vessel into a manufacturing vessel. Typically, in batches prepared for pharmaceutical use, each filled canister is check-weighed, coded with a batch number and packed into a tray for storage before release testing.

In an alternative process, an aliquot of the liquified formulation is added to an open canister under conditions which are sufficiently cold that the formulation does not vaporise, and then a metering valve crimped onto the canister.

Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise, for example a valve actuator and a cylindrical or cone-like passage through which medicament may be delivered from the filled canister via the metering valve to the nose or mouth of a patient eg. a mouthpiece actuator. Metered dose inhalers are designed to deliver a fixed unit dosage of medicament per actuation or 'puff', for example in the range of 10 to 5000 µg medicament per puff.

In a typical arrangement the valve stem is seated in a nozzle block which has an orifice leading to an expansion chamber. The expansion chamber has an exit orifice which extends into the mouthpiece. Actuator (exit) orifice diameters in the range 0.1–0.45 mm are generally suitable eg 0.15, 0.22, 0.25, 0.30, 0.33 or 0.42 mm. We have found that it is advantageous to use a small diameter eg 0.25 mm or less, particularly 0.22 mm since this tends to result in a higher FPM and lower throat deposition. 0.15 mm is also particularly suitable. The dimensions of the orifice should not be so small that blockage of the jet occurs.

Actuator jet lengths are typically in the range 0.30–1.7 mm eg 0.30, 0.65 or 1.50 mm. for buccal administration.

The precise shape and dimensions of the actuator will be adapted for topical administration to the lung or nose as appropriate.

The desirable biological properties of the compound of formula (I) are explained as follows:

Compound (I) undergoes highly efficient hepatic metabolism to yield the 17-β carboxylic acid (X) as the sole major metabolite in rat and human in vitro systems. This metabolite has been synthesised and demonstrated to be >1000 fold less active than the parent compound in in vitro functional glucocorticoid assays.

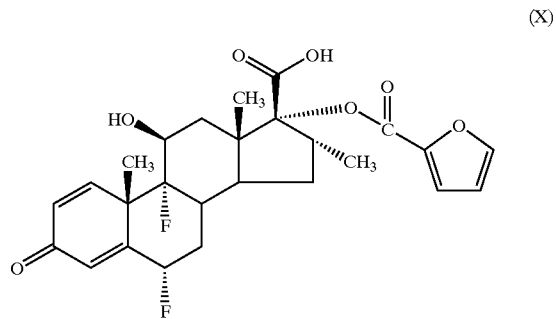

(X)

This efficient hepatic metabolism is reflected by in vivo data in the rat, which have demonstrated plasma clearance at a rate approaching hepatic blood flow and an oral bioavailability of <1%, consistent with extensive first-pass metabolism.

In vitro metabolism studies in human hepatocytes have demonstrated that compound (I) is metabolised in an identical manner to fluticasone propionate but that conversion of (I) to the inactive acid metabolite occurs approximately 5-fold more rapidly than with fluticasone propionate. This very efficient hepatic inactivation would be expected to minimise systemic exposure in man leading to an improved safety profile.

Inhaled steroids are also absorbed through the lung and this route of absorption makes a significant contribution to systemic exposure. Reduced lung absorption could therefore provide an improved safety profile. Studies with compound (I) have shown significantly lower exposure to compound (I) than with fluticasone propionate after dry powder delivery to the lungs of anaesthetised pigs.

Examples of disease states in which the compound of the invention has utility include inflammatory conditions of the nose, throat or lungs such as asthma (including allergen-induced asthmatic reactions), rhinitis (including hayfever), nasal polyps, chronic obstructive pulmonary disease (COPD), interstitial lung disease, and fibrosis.

The formulation comprising a compound of formula (I) and solvates thereof is expected to be most useful in the treatment of inflammatory disorders of the respiratory tract eg asthma or COPD, and rhinitis.

It will be appreciated by those skilled in the art that reference herein to treatment extends to prophylaxis as well as the treatment of established conditions.

As mentioned above, the compound of formula (I) is useful in human or veterinary medicine, in particular as an anti-inflammatory and anti-allergic agent.

There is thus provided as a further aspect of the invention a formulation comprising the compound of formula (I) or a physiologically acceptable solvate thereof for use in human or veterinary medicine, particularly in the treatment of patients with inflammatory and/or allergic conditions.

According to another aspect of the invention, there is provided the use of a formulation comprising the compound of formula (I) or physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a formulation comprising the compound of formula (I) or physiologically acceptable solvate thereof.

Further, there is provided a process for the preparation of such pharmaceutical compositions which comprises mixing the ingredients.

Aerosol formulations are preferably arranged so that each metered dose or "puff" of aerosol contains 1 μg–2000 μg eg 20 μg–2000 μg, preferably about 20 μg–500g of a compound of formula (I) optionally in combination with another therapeutically active ingredient. Administration may be once daily or several times daily, for example 2, 3, 4 or 8 times, giving for example 1, 2 or 3 doses each time. Preferably the compound of formula (I) is delivered once or twice daily, especially once daily. The overall daily dose with an aerosol for adminstration to the lung in the treatment of eg asthma will typically be within the range 10 μg–10 mg eg 50 μg–10 mg preferably, 50 μg–2000 μg eg 50 μg–500 μg. The overall daily dose with an aerosol for adminstration to the nose in the treatment of eg rhinitis per nostril will typically be within the range 10 μg–5 mg eg 25 μg–1 mg preferably, 25 μg–500 μg eg 25 μg–75 μg, such as 50 μg.

The volume of formulation metered per actuation will typically be in the range 25–100 μl eg 25, 50, 63 or 100 μl, especially around 100 μl.

The compound of formula (I) will typically be employed in solution at a concentration of 0.005–0.5% w/w based on weight of formulation, especially 0.01–0.3% w/w.

Since the compound of formula (I) is long-acting, preferably the compound will be delivered once-per-day and the dose will be selected so that the compound has a therapeutic effect in the treatment of respiratory disorders (eg asthma, COPD or rhinitis) over 24 hours or more.

The pharmaceutical compositions according to the invention may also be used in combination with another therapeutically active agent, for example, a $\beta_2$ adrenoreceptor agonist, an anti-histamine or an anti-allergic. The invention thus provides, in a further aspect, a combination comprising the compound of formula (I) or a physiologically acceptable solvate thereof together with another therapeutically active agent, for example, a $\beta_2$-adrenoreceptor agonist, an anti-histamine or an anti-allergic.

Examples of $\beta_2$-adrenoreceptor agonists include salmeterol (eg as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Pharmaceutical compositions employing combinations with long-acting $\beta_2$-adrenoreceptor agonists (eg salmeterol and salts thereof) are particularly preferred, especially those which have a therapeutic effect (eg in the treatment of asthma or COPD, particularly asthma) over 24 hours or more.

Since the compound of formula (I) is long-acting, preferably the composition comprising the compound of formula (I) and the long-acting $\beta_2$-adrenoreceptor agonists will be delivered once-per-day and the dose of each will be selected so that the composition has a therapeutic effect in the treatment of respiratory disorders effect (eg in the treatment of asthma or COPD, particularly asthma) over 24 hours or more.

Examples of anti-histamines include methapyrilene or loratadine.

Other suitable combinations include, for example, other anti-inflammatory agents eg NSAIDs (eg sodium cromoglycate, nedocromil sodium, PDE4 inhibitors, leukotriene antagonists, iNOS inhibitors, tryptase and elastase inhibitors, beta-2 integrin antagonists and adenosine 2a agonists)) or antiinfective agents (eg antibiotics, antivirals). Also of particular interest is use of the compound of formula (I) or a physiologically acceptable solvate thereof in combination with a phosphodiesterase 4 (PDE4) inhibitor eg cilomilast or a salt thereof.

The preferred route of administration for inflammatory disorders of the respiratory tract will generally be administration by inhalation. For treatment of rhinitis the route of administration will generally be topically to the nasal mucosa.

Further, there is provided a process for the preparation of such pharmaceutical compositions which comprises mixing the ingredients.

The individual compounds of such combinations may be administered either sequentially in separate pharmaceutical compositions as well as simultaneously in combined pharmaceutical formulations. Appropriate doses of known therapeutic agents will be readily appreciated by those skilled in the art.

A process for preparing a compound of formula (I) will be described as follows:

A process for preparing a compound of formula (I) comprises alkylation of a thioacid of formula (II)

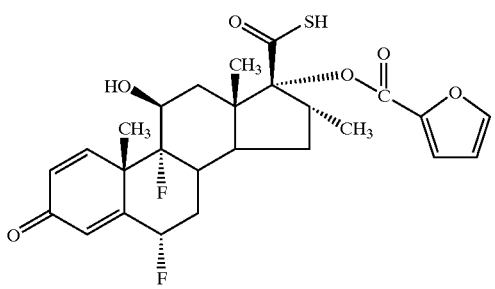

(II)

or a salt thereof.

In this process the compound of formula (II) may be reacted with a compound of formula FCH$_2$L wherein L represents a leaving group (eg a halogen atom, a mesyl or tosyl group or the like) for example, an appropriate fluoromethyl halide under standard conditions. Preferably, the fluoromethyl halide reagent is bromofluoromethane. Preferably the compound of formula (II) is employed as a salt, particularly the salt with diisopropylethylamine.

In a preferred process for preparing the compound of formula (I), the compound of formula (II) or a salt thereof is treated with bromofluoromethane optionally in the presence of a phase transfer catalyst. A preferred solvent is methylacetate, or more preferably ethylacetate, optionally in the presence of water. The presence of water improves solubility of both starting material and product and the use of a phase transfer catalyst results in an increased rate of reaction. Examples of phase transfer catalysts that may be employed include (but are not restricted to) tetrabutylammonium bromide, tetrabutylammonium chloride, benzyltributylammonium bromide, benzyltributylammonium chloride, benzyltriethylammonium bromide, methyltributylammonium chloride and methyltrioctylammonium chloride. THF has also successfully been employed as solvent for the reaction wherein the presence of a phase transfer catalyst again provides a significantly faster reaction rate. Preferably the product present in an organic phase is washed firstly with aqueous acid eg dilute HCl in order to remove amine compounds such as triethylamine and diisopropylethylamine and then with aqueous base eg sodium bicarbonate in order to remove any unreacted precursor compound of formula (II).

Compound of formula (I) in unsolvated form may be prepared by a process comprising:

(a) Crystallising the compound of formula (I) in the presence of a non-solvating solvent such as ethanol, methanol, water, ethyl acetate, toluene, methylisobutylketone or mixtures thereof; or (b) Desolvating a compound of formula (I) in solvated form (eg in the form of a solvate with acetone, isopropanol, methylethylketone, DMF or tetrahydrofuran) eg by heating.

In step (b) the desolvation will generally be performed at a temperature exceeding 50° C. preferably at a temperature exceeding 100° C. Generally heating will be performed under vacuum.

Compound of formula (I) in unsolvated form has been found to exist in 3 crystalline polymorphic forms, Forms 1, 2 and 3, although Form 3 may be an unstable variant of Form 2. The Forms are characterised by their X-ray diffraction (XRPD) patterns Broadly speaking the Forms are characterised in their XRPD profiles as follows:

Form 1: Peak at around 18.9 degrees 2Theta

Form 2: Peaks at around 18.4 and 21.5 degrees 2Theta

Form 3: Peaks at around 18.6 and 19.2 degrees 2Theta.

Forms 1 appears likely to be the thermodynamically most stable form since Forms 2 and 3 are converted into Form 1 on heating.

A process for preparing a compound of formula (I) as unsolvated Form 1 polymorph comprises dissolving compound of formula (I) in methylisobutylketone, ethyl acetate or methyl acetate and producing compound of formula (I) as unsolvated Form 1 by addition of a non-solvating anti-solvent such as iso-octane or toluene.

According to a first preferred embodiment of this process the compound of formula (I) may be dissolved in ethyl acetate and compound of formula (I) as unsolvated Form 1 polymorph may be obtained by addition of toluene as anti-solvent. In order to improve the yield, preferably the ethyl acetate solution is hot and once the toluene has been added the mixture is distilled to reduce the content of ethyl acetate.

According to a second preferred embodiment of this process the compound of formula (I) may be dissolved in methylisobutylketone and compound of formula (I) as unsolvated Form 1 polymorph may be obtained by addition of isooctane as anti-solvent.

Compound of formula (I) in solvated form may be prepared by crystallising the compound of formula (I) from a solvating solvent such as acetone or tetrahydrofuran (THF).

Preferably in processes for preparing formulations of the invention, the compound of formula (I) will be employed in unsolvated form, typically unsolvated Form 1.

Compounds of formula (II) may be prepared from the corresponding 17α-hydroxyl derivative of formula (III):

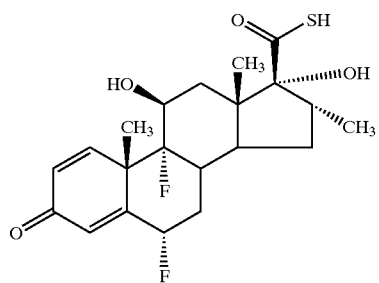

(III)

using for example, the methodology described by G. H. Phillipps et al., (1994) Journal of Medicinal Chemistry, 37, 3717–3729. For example the step typically comprises the addition of a reagent suitable for performing the esterification eg an activated derivative of 2-furoic acid such as an activated ester or preferably a 2-furoyl halide eg 2-furoyl chloride (employed in at least 2 times molar quantity relative to the compound of formula (III)) in the presence of an organic base eg triethylamine. The second mole of 2-furoyl chloride reacts with the thioacid moiety in the compound of formula (III) and needs to be removed eg by reaction with an amine such as diethylamine.

This method suffers disadvantages, however, in that the resultant compound of formula (II) is not readily purified of contamination with the by-product 2-furoyldiethylamide. We have therefore invented several improved processes for performing this conversion.

In a first such improved process we have discovered that by using a more polar amine such as diethanolamine, a more water soluble by-product is obtained (in this case 2-furoyldiethanolamide) which permits compound of formula (II) or a salt thereof to be produced in high purity since the by-product can efficiently be removed by water washing.

Thus we provide a process for preparing a compound of formula (II) which comprises:
(a) reacting a compound of formula (III) with an activated derivative of 2-furoic acid as in an amount of at least 2 moles of the activated derivative per mole of compound of formula (III) to yield a compound of formula (IIA)

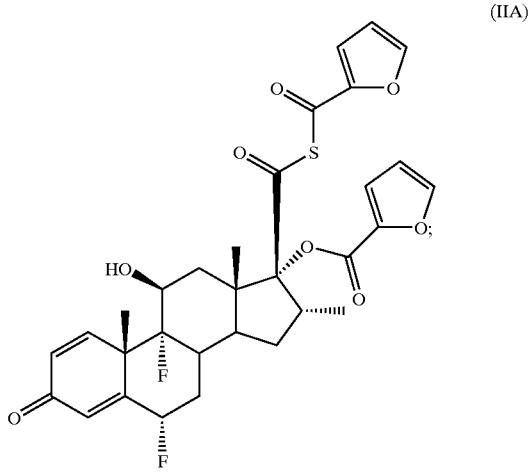

(IIA)

and
(b) removal of the sulphur-linked 2-furoyl moiety from compound of formula (IIA) by reaction of the product of step (a) with an organic primary or secondary amine base capable of forming a water soluble 2-furoyl amide.

In two particularly convenient embodiments of this process we also provide methods for the efficient purification of the end product which comprise either
(c1) when the product of step (b) is dissolved in a substantially water immiscible organic solvent, purifying the compound of formula (II) by washing out the amide by-product from step (b) with an aqueous wash, or
(c2) when the product of step (b) is dissolved in a water miscible solvent, purifying the compound of formula (II) by treating the product of step (b) with an aqueous medium so as to precipitate out pure compound of formula (II) or a salt thereof.

In step (a) preferably the activated derivative of 2-furoic acid may be an activated ester of 2-furoic acid, but is more preferably a 2-furoyl halide, especially 2-furoyl chloride. A suitable solvent for this reaction is ethylacetate or methylacetate (preferably methylacetate) (when step (c1) may be followed) or acetone (when step (c2) may be followed). Normally an organic base eg triethylamine will be present. In step (b) preferably the organic base is diethanolamine. The base may suitably be dissolved in a solvent eg methanol. Generally steps (a) and (b) will be performed at reduced temperature eg between 0 and 5° C. In step (c1) the aqueous wash may be water, however the use of brine results in higher yields and is therefore preferred. In step (c2) the aqueous medium is for example a dilute aqueous acid such as dilute HCl.

We also provide an alternative process for preparing a compound of formula (II) which comprises:
(a) reacting a compound of formula (III) with an activated derivative of 2-furoic acid in an amount of at least 2 moles of activated derivative per mole of compound of formula (III) to yield a compound of formula (IIA); and
(b) removal of the sulphur-linked 2-furoyl moiety from compound of formula (IIA) by reaction of the product of step (a) with a further mole of compound of formula (III) to give two moles of compound of formula (II).

In step (a) preferably the activated derivative of 2-furoic acid may be an activated ester of 2-furoic acid, but is more preferably a 2-furoyl halide, especially 2-furoyl chloride. A suitable solvent for his step is acetone. Normally an organic base eg triethylamine will be present. In step (b) a suitable solvent is DMF or dimethylacetamide. Normally an organic base eg triethylamine will be present. Generally steps (a) and (b) will be performed at reduced temperature eg between 0 and 5° C. The product may be isolated by treatment with acid and washing with water.

This aforementioned process is very efficient in that it does not produce any furoylamide by-product (thus affording inter alia environmental advantages) since the excess mole of furoyl moiety is taken up by reaction with a further mole of compound of formula (II) to form an additional mole of compound of formula (II).

Further general conditions for the conversion of compound of formula (III) to compound of formula (II) in the two processes just described will be well known to persons skilled in the art.

According to a preferred set of conditions, however, we have found that the compound of formula (II) may advantageously be isolated in the form of a solid crystalline salt. The preferred salt is a salt formed with a base such as triethylamine, 2,4,6-trimethylpyridine, diisopropylethylamine or N-ethylpiperidine. Such salt forms of compound of formula (II) are more stable, more readily filtered and dried and can be isolated in higher purity than the free thioacid. The most preferred salt is the salt formed with diisopropylethylamine. The triethylamine salt is also of interest.

Compounds of formula (III) may be prepared in accordance with procedures described in GB 2088877B. Compounds of formula (III) may also be prepared by a process comprising the following steps:

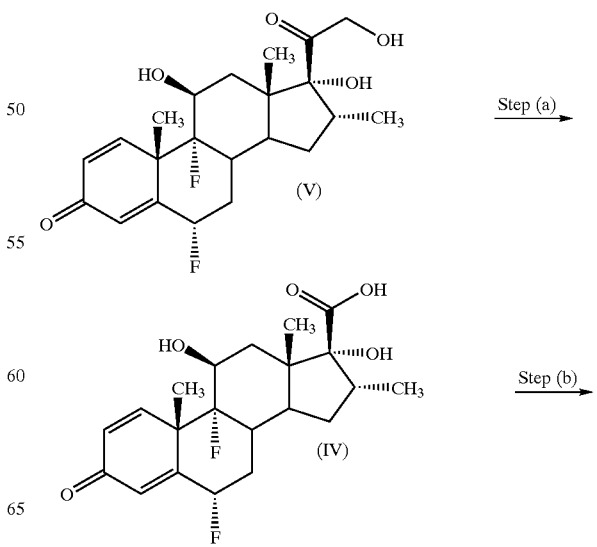

-continued

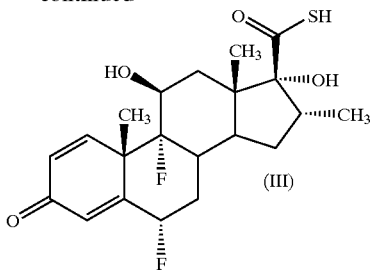

Step (a) comprises oxidation of a solution containing the compound of formula (V). Preferably, step (a) will be performed in the presence of a solvent comprising methanol, water, tetrahydrofuran, dioxan or diethylene glygol dimethylether. So as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1wt.), more preferably between 4 and 6 vol., especially 5 vol. Preferably the oxidising agent is present in an amount of 1–9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, eg one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. eg for 2 hours. The compound of formula (IV) may be isolated by recrystallisation from the reaction mixture by addition of an anti-solvent. A suitable anti-solvent for compound of formula (IV) is water. Surprisingly we have discovered that it is highly desirable to control the conditions under which the compound of formula (IV) is precipitated by addition of anti-solvent eg water. When the recrystallisation is performed using chilled water (eg water/ice mixture at a temperature of 0–5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice. By contrast when conditions of around 10° C. or higher are used (eg around ambient temperature) a granular product of a sand like consistency which is very easily filtered is produced. Under these conditions, crystallisation typically commences after around 1 hour and is typically completed within a few hours (eg 2 hours). Without being limited by theory we believe that this granular product contains little or no solvated solvent within the crystal lattice.

Step (b) will typically comprise the addition of a reagent suitable for converting a carboxylic acid to a carbothioic acid eg using hydrogen sulphide gas together with a suitable coupling agent eg carbonyldiimidazole (CDI) in the presence of a suitable solvent eg dimethylformamide.

The advantages of the aerosol formulation of the compound of formula (I) may include the fact that the substance appears to demonstrate excellent anti-inflammatory properties, with predictable pharmacokinetic and pharmacodynamic behaviour, good bioavailabiity, faster onset of action, with an attractive side-effect profile, long duration of action, and is compatible with a convenient regime of treatment in human patients, in particular being amendable to once-per day dosing. Further advantages may include the fact that the formulation has desirable physical and chemical properties which allow for ready manufacture and storage.

The following non-limiting Examples illustrate the invention:

EXAMPLES

General $^1$H-nmr spectra were recorded at 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), ddd (doublet of doublet of doublets), dt (doublet of triplets) and b (broad). Biotage refers to prepacked silica gel cartridges containing KP-Sil run on flash 12i chromatography module. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 min 0%B, 0.7–4.2 min 100%B, 4.2–5.3 min 0%B, 5.3–5.5 min 0%B at a flow rate of 3 ml/min. The mass spectra were recorded on a Fisons VG Platform spectrometer using electrospray positive and negative mode (ES+ve and ES−ve).

Intermediates

Intermediate 1: 6α, 9α-Difluoro-17α-[(2-furanylcarbonyl)oxy]-11β-hydroxy-16α-methyl-3-oxo-androsta-1,4-diene-17β-carbothioic acid diisopropylethylamine salt A stirred suspension of 6α, 9α-difluoro-11β, 17α-dihydroxy-16α-methyl-3-oxo-androsta-1,4-diene-17β-carbothioic acid (prepared in accordance with the procedure described in GB 2088877B) (49.5 g) in methylacetate (500 ml) is treated with triethylamine (35 ml) maintaining a reaction temperature in the range 0-5° C. 2-Furoyl chloride (25 ml) is added and the mixture stirred at 0-5° C. for 1 hour. A solution of diethanolamine (52.8 g) in methanol (50 ml) is added and the mixture stirred at 0–5° C. for at least 2 hours. Dilute hydrochloric acid (approx 1M, 550 ml) is added maintaining a reaction temperature below 15° C. and the mixture stirred at 15° C. The organic phase is separated and the aqueous phase is back extracted with methyl acetate (2×250 ml). All of the organic phases are combined, washed sequentially with brine (5 ×250 ml) and treated with di-isopropylethylamine (30 ml). The reaction mixture is concentrated by distillation at atmospheric pressure to an approximate volume of 250 ml and cooled to 25–30° C. (crystallisation of the desired product normally occurs during distillation/subsequent cooling). Tertiary butyl methyl ether (TBME) (500 ml) is added, the slurry further cooled and aged at 0–5° C. for at least 10 minutes. The product is filtered off, washed with chilled TBME (2×200 ml) and dried under vacuum at approximately 40–50° C. (75.3 g, 98.7%). NMR ($CDCl_3$) δ: 7.54–7.46 (1H, m), 7.20–7.12 (1H, dd), 7.07–6.99 (1H, dd), 6.48–6.41 (2H, m), 6.41–6.32 (1H, dd), 5.5 (1H, dddd $^2J_{H-F}$ 50 Hz), 4.45–4.33(1H, bd), 3.92–3.73 (3H, bm), 3.27–3.14 (2H, q), 2.64–2.12 (5H, m), 1.88–1.71 (2H, m), 1.58–1.15 (3H, s), 1.50–1.38 (15H, m), 1.32–1.23 (1H, m), 1.23–1.15 (3H s), 1.09–0.99 (3H, d).
Intermediate 2: 6α, 9α-Difluoro-17α-[(2-furanylcarbonyl)oxy]11β-hydroxy-16α-methyl-3-oxo-androsta-1,4-diene-17β-carbothioic acid S-fluoromethyl ester
Unsolvated Form 1

A mobile suspension of Intermediate 1 (12.61 g, 19.8 mmol) in ethyl acetate (230 ml) and water (50ml) is treated with a phase transfer catalyst (benzyltributylammonium chloride, 10 mol %), cooled to 3° C. and treated with bromofluoromethane (1.10 ml, 19.5 mmol, 0.98 equivalents), washing in with prechilled (0° C.) ethyl acetate (EtOAc) (20 ml). The suspension is stirred overnight, allowing to warm to 17° C. The aqueous layer is separated and the organic phase is sequentially washed with 1 M HCl (50 ml), 1% w/v NaHCO$_3$ solution (3×50 ml) and water (2×50 ml). The ethylacetate solution is distilled at atmospheric pressure until the distillate reaches a temperature of approximately 73° C. at which point toluene (150 ml) is added. Distillation is continued at atmospheric pressure until all remaining EtOAc has been removed (approximate distillate temperature 103° C.). The resultant suspension is cooled and aged at <10° C. and filtered off. The bed is washed with toluene (2×30 ml) and the product oven dried under vacuum at 60° C. to constant weight to yield the title compound (8.77 g, 82%) LCMS retention time 3.66 min, m/z 539 MH$^+$, NMR δ (CDCl$_3$) includes 7.60 (1H, m), 7.18–7.11 (2H, m), 6.52 (1H, dd, J 4.2 Hz), 6.46 (1H, s), 6.41 (1H, dd, J 10, 2 Hz), 5.95 and 5.82 (2H dd, J 51, 9 Hz), 5.48 and 5.35 (1H, 2m), 4.48 (1H, m), 3.48 (1H, m), 1.55 (3H, s), 1.16 (3H, s), 1.06 (3H, d, J 7 Hz).

Pharmacological Activity
In Vitro Pharmacological Activity

Pharmacological activity was assessed in a functional in vitro assay of glucocorticoid agonist activity which is generally predictive of anti-inflammatory or anti-allergic activity in vivo.

For the experiments in this section, compound of formula (I) was used as unsolvated Form 1 (Intermediate 2).

The functional assay was based on that described by K. P.Ray et al., Biochem J. (1997), 328, 707–715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which EC$_{50}$ values were estimated.

In this test the compound of formula (I) showed an EC$_{50}$ value of <1nM.

The glucocorticoid receptor (GR) can function in at least two distinct mechanisms, by upregulating gene expression through the direct binding of GR to specific sequences in gene promoters, and by downregulating gene expression that is being driven by other transcription factors (such as NFκB or AP-1) through their direct interaction with GR.

In a variant of the above method, to monitor these functions, two reporter plasmids have been generated and introduced separately into A549 human lung epithelial cells by transfection. The first cell line contains the firefly luciferase reporter gene under the control of a synthetic promoter that specifically responds to activation of the transcription factor NFκB when stimulated with TNFα. The second cell line contains the renilla luciferase reporter gene under the control of a synthetic promotor that comprises 3 copies of the consensus glucocorticoid response element, and which responds to direct stimulation by glucocorticoids. Simultaneous measurement of transactivation and transrepression was conducted by mixing the two cell lines in a 1:1 ratio in 96 well plate (40,000 cells per well) and growing overnight at 37° C. Test compounds were dissolved in DMSO, and added to the cells at a final DMSO concentration of 0.7%. After incubation for 1 h 0.5 ng/ml TNFα (R&D Systems) was added and after a further 15 hours at 37° C., the levels of firefly and renilla luciferase were measured using the Packard Firelite kit following the manufacturers' directions. Dose response curves were constructed from which EC$_{50}$ values were determined.

|  | Transactivation (GR) ED$_{50}$ (nM) | Transrepression (NFκB) ED$_{50}$ (nM) |
| --- | --- | --- |
| Compound of Formula (I) | 0.06 | 0.20 |
| Metabolite (X) | >250 | >1000 |
| Fluticasone propionate | 0.07 | 0.16 |

In vivo Pharmacological Activity

Pharmacological activity in vivo was assessed in an ovalbumin sensitised Brown Norway rat eosinophilia model. This model is designed to mimic allergen induced lung eosinophilia, a major component of lung inflammation in asthma.

For the experiments in this section, compound of formula (I) was used as unsolvated Form 1.

Compound of formula (I) produced dose dependant inhibition of lung eosinophilia in this model after dosing as an intra-tracheal (IT) suspension in saline 30 min prior to ovalbumin challenge. Significant inhibition is achieved after a single dose of 30 μg of compound of formula (I) and the response was significantly (p=0.016) greater than that seen with an equivalent dose of fluticasone propionate in the same study (69% inhibition with compound of formula (I) vs 41% inhibition with fluticasone propionate).

In a rat model of thymus involution 3 daily IT doses of 100 μg of compound (I) induced significantly smaller reductions in thymus weight (p=0.004) than an equivalent dose of fluticasone propionate in the same study (67% reduction of thymus weight with compound (I) vs 78% reduction with fluticasone propionate).

Taken together these results indicate a superior therapeutic index for compound (I) compared to fluticasone propionate.

In Vitro Metabolism in Rat and Human Hepatocytes

Incubation of compound (I) with rat or human hepatocytes shows the compound to be metabolised in an identical manner to fluticasone propionate with the 17-β carboxylic acid (X) being the only significant metabolite produced. Investigation of the rate of appearance of this metabolite on incubation of compound (I) with human hepatocytes (37° C., 10 μM drug concentration, hepatocytes from 3 subjects, 0.2 and 0.7 million cells/mL) shows compound (I) to be metabolised ca. 5-fold more rapidly than fluticasone propionate:

| Subject number | Cell density (million cells/mL) | 17-β acid metabolite production (pmol/h) | |
|---|---|---|---|
| | | Compound (I) | Fluticasone propionate |
| 1 | 0.2 | 48.9 | 18.8 |
| 1 | 0.7 | 73.3 | 35.4 |
| 2 | 0.2 | 118 | 9.7 |
| 2 | 0.7 | 903 | 23.7 |
| 3 | 0.2 | 102 | 6.6 |
| 3 | 0.7 | 580 | 23.9 |

Median metabolite production 102–118 pmol/h for compound (I) and 18.8–23.0 pmol/h for fluticasone propionate.

Pharmacokinetics after Intravenous (IV) and Oral Dosing in Rats

Compound (I) was dosed orally (0.1 mg/kg) and IV (0.1 mg/kg) to male Wistar Han rats and pharmacokinetic parameters determined. Compound (I) showed negligible oral bioavailability (0.9%) and plasma clearance of 47.3 mL/min/kg, approaching liver blood flow (plasma clearance of fluticasone propionate=45.2 mL/min/kg).

Pharmacokinetics after Intra-Tracheal Dry Powder Dosing in the Pig

Anaesthetised pigs (2) were dosed intra-tracheally with a homogenous mixture of compound (I) (1 mg) and fluticasone propionate (1 mg) as a dry powder blend in lactose (10% w/w). Serial blood samples were taken for up to 8 h following dosing. Plasma levels of compound (I) and fluticasone propionate were determined following extraction and analysis using LC-MS/MS methodology, the lower limits of quantitation of the methods were 10 and 20 pg/mL for compound (I) and fluticasone propionate respectively. Using these methods compound (I) was quantifiable up to 2 hours after dosing and fluticasone propionate was quantifiable up to 8 hours after dosing. Maximum plasma concentrations were observed for both compounds within 15 min after dosing. Plasma half-life data obtained from IV dosing (0.1 mg/kg) was used to calculate AUC (0-inf) values for compound (I). This compensates for the plasma profile of Compound (I) only being defined up to 2 hours after an IT dose and removes any bias due to limited data between compound (I) and fluticasone propionate.

$C_{max}$ and AUC (0-inf) values show markedly reduced systemic exposure to compound (I) compared to fluticasone propionate:

| | Cmax (pg/mL) | | AUC (0-inf) (hr. pg/mL) | |
|---|---|---|---|---|
| | Pig 1 | Pig 2 | Pig 1 | Pig 2 |
| Compound of Formula (I) | 117 | 81 | 254 | 221 |
| Fluticasone propionate | 277 | 218 | 455 | 495 |

The pharmacokinetic parameters for both compound (I) and fluticasone propionate were the same in the anaesthetised pig following intravenous administration of a mixture of the two compounds at 0.1 mg/kg. The clearance of these two glucocorticoids is similar is this experimental pig model.

EXAMPLES

In the foregoing Examples 1–3, the oligolactic acid derivative may be prepared according to the methods of WO94/21229. The oligolactic acid that may be used is prepared from either racemic lactic acid and has a median chain length of n=9 with an acetyl cap on the hydroxy terminus.

Example 1

Aerosol formulation containing 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester An aluminium canister may be filled with a solution formulation composed as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester, unsolvated Form 1 prepared according to Intermediate 2 | 12.5 μg |
| oligolactic acid derivative | 600 μg |
| 1,1,1,2-tetrafluoroethane: | to 100 μl |
| (amounts per actuation) | | in a total amount suitable for 120 actuations and the canister may be fitted with a metering valve adapted to dispense 100 μl per actuation.

The canister may be fitted into an actuator suitable for topical delivery to the lung (Valois).

Example 2

Nasal formulation containing 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester An aluminium canister may be filled with a solution formulation for intranasal delivery as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester, unsolvated Form 1 prepared according to Intermediate 2: | 12.5 μg |
| oligolactic acid derivative | 600 μg |
| 1,1,1,2-tetrafluoroethane | to 100 μl |
| (amounts per actuation) | | in a total amount suitable for 120 actuations and the canister may be fitted with a metering valve adapted to dispense 100 μl per actuation.

The canister may be fitted into a nasal actuator (Valois).

Example 3

Nasal formulation containing 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester An aluminium canister may be filled with a solution formulation for intranasal delivery as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester, unsolvated Form 1 prepared according to Intermediate 2: | 50 μg |
| oligolactic acid derivative | 1200 μg |
| 1,1,1,2-tetrafluoroethane | to 100 μl |
| (amounts per actuation) | | in a total amount suitable for 120 actuations and the canister may be fitted with a metering valve adapted to dispense 100 µl per actuation.

The canister may be fitted into a nasal actuator (Valois).

Example 4–6

Examples 1–3 may be repeated employing an oligolactic acid derivative prepared form L-lactic acid instead of racemic lactic acid.

Example 7
Nasal formulation containing 6α, 9α-Difluoro-17α-[(2-furanylcarbonyl)oxy]11β-hydroxy-16α-methyl-3-oxo-androsta-1,4-diene-17β-carbothioic acid S-fluoromethyl ester An aluminium canister may be filled with a solution formulation for intranasal delivery as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester, unsolvated Form 1 prepared according to Intermediate 2: | 0.05% w/v |
| ethanol | 10% w/w |
| 1,1,1,2-tetrafluoroethane | to 100% | in a total amount suitable for 120 actuations and the canister may be fitted with a metering valve adapted to dispense 50 µl per actuation. This formulation is suitable for delivering 25 pg of compound of formula (I) per actuation.

The canister may be fitted into a nasal actuator (Valois).

Example 8
Aerosol formulation containing 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester An aluminium canister may be filled with a solution formulation composed as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester, unsolvated Form 1 prepared according to Intermediate 2 | 0.1% w/v |
| ethanol | 15% w/w |
| glycerol | 1% w/w |
| 1,1,1,2-tetrafluoroethane: | to 100% | in a total amount suitable for 120 actuations and the canister may be fitted with a metering valve adapted to dispense 50 µl per actuation. This formulation is suitable for delivering 50 µg of compound of formula (1) per actuation. The canister may be fitted into an actuator suitable for topical delivery to the lung (Valois).

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The patents and patent applications described in this application are herein incorporated by reference.

What is claimed is:
1. A pharmaceutical aerosol formulation comprising (i) a compound of formula (I)

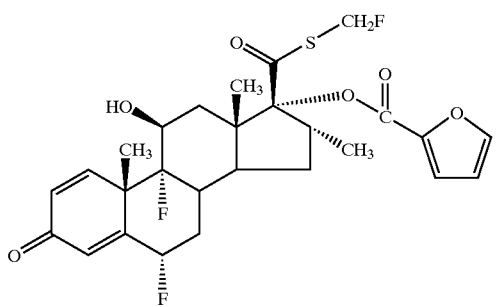

(I)

or a solvate thereof as medicament, (ii) a liquefied hydrofluoroalkane (HFA) gas as propellant; and characterised in that the compound of formula (I) or a solvate thereof is completely dissolved in the formulation.

2. A formulation according to claim 1 which contains a hydroxy containing co-solvent liquid as solubilising agent.

3. A formulation according to claim 2 wherein the solubilsing agent is ethanol.

4. A formulation according to claim 1 further comprising a low volatility component.

5. A formulation according to claim 4 wherein the low volatility component is glycerol.

6. A formulation according to claim 1 wherein the propellant gas is 1,1,1,2-tetrafluoroethane.

7. A pharmaceutical aerosol formulation according to claim 1 comprising (i) a compound of formula (I)

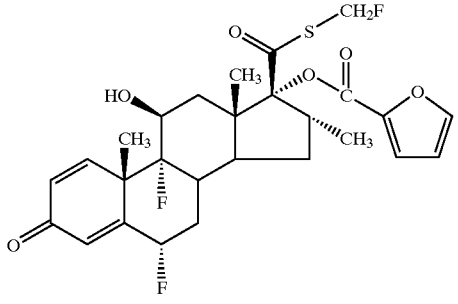

(I)

or a solvate thereof as medicament, (ii) 1,1,1,2-tetrafluoroethane as propellant, (iii) a solubilising agent to assist the solubilisation of the medicament in the propellant and (iv) optionally a low volatility component; characterised in that the compound of formula (I) or a solvate thereof is completely dissolved in the formulation.

8. A formulation according to claim 7 which contains ethanol as solubilising agent and glycerol as low volatility component.

9. A formulation according to claim 1 wherein the solubilising agent is an oligolactic acid or derivative thereof.

10. A formulation according to claim 9 wherein the solubilising agent is a compound of formula (IIA)

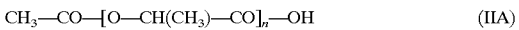

$$CH_3-CO-[O-CH(CH_3)-CO]_n-OH \qquad (IIA)$$

or a derivative thereof, wherein n is an integer from 3 to 15.

11. A canister comprising a container containing a formulation according to claim 1 and fitted with a metering valve.

12. A canister comprising a container containing a formulation according to claim 7 and fitted with a metering valve.

13. A canister comprising a container containing a formulation according to claim 9 and fitted with a metering valve.

14. A metered dose inhaler comprising a canister according to claim 11 fitted with an actuator adapted for topical administration of the formulation to the lung.

15. A metered dose inhaler comprising a canister according to claim 11 fitted with an actuator adapted for topical administration of the formulation to the nose.

16. A metered dose inhaler comprising a canister according to claim 12 fitted with an actuator adapted for topical administration of the formulation to the lung.

17. A metered dose inhaler comprising a canister according to claim 12 fitted with an actuator adapted for topical administration of the formulation to the nose.

18. A metered dose inhaler comprising a canister according to claim 13 fitted with an actuator adapted for topical administration of the formulation to the lung.

19. A metered dose inhaler comprising a canister according to claim 13 fitted with an actuator adapted for topical administration of the formulation to the nose.

* * * * *